United States Patent [19]
Williams et al.

[11] Patent Number: 5,935,120
[45] Date of Patent: Aug. 10, 1999

[54] CATHETER AND METHOD FOR EVALUATING COMPETENCY OF MITRAL VALVE

[75] Inventors: Ronald A. Williams, Grand Rapids, Mich.; Peter J. K. Starek, Chapel Hill, N.C.

[73] Assignee: Medtronics, Inc., Minneapolis, Minn.

[21] Appl. No.: 08/978,227

[22] Filed: Nov. 25, 1997

[51] Int. Cl.$^6$ ................................................. A61M 25/00
[52] U.S. Cl. ........................ 604/500; 604/523; 604/532; 606/194
[58] Field of Search ................................ 604/500, 503, 604/505, 507, 508, 523, 528, 532, 524, 264; 606/192–194

[56] References Cited

U.S. PATENT DOCUMENTS

| | | | |
|---|---|---|---|
| 5,084,010 | 1/1992 | Plaia et al. | 606/194 |
| 5,267,982 | 12/1993 | Sylvanowicz | 604/523 |
| 5,333,609 | 8/1994 | Bedingham et al. | 604/528 X |
| 5,358,493 | 10/1994 | Schweich, Jr et al. | 604/500 |

OTHER PUBLICATIONS

Akins, et al., Mitral Valve Reconstruction Versus Replacement for Degenerative or Ischemic Mitral Regurgitation, Ann. Thorac. Surg. 1994, vol. 58, pp. 668–676.

Hetzer, et al., Intraoperative Assessment of the Reconstructed Mitral Valve Using a Low Presure Crystalloid Infusion, Thorac. Cardiovasc. Surg. 1981 vol. 29, pp. 100–104.

Grossi, et al., Severe Calcification Does Not Affect Long-–Term Outccome of Mitral Valve Repair, Ann. Thorac. Surg. 1994, vol. 58, pp. 685–688.

Sundt, et al., Alternative Technique for Assessment and Repair of the Mitral Valve, Ann. Thorac. Surg. 1996, vol. 61, pp. 1552–1554.

Miyamoto, Transatrial Atrioventricular Valve Testing in the Beating, Fully Loaded Heart, Ann. Thorac. Surg. 1996, vol. 61, pp. 1265–1266.

*Primary Examiner*—John D. Yasko
*Attorney, Agent, or Firm*—Foley & Lardner

[57] ABSTRACT

A catheter for evaluating the competency of a mitral valve has a main lumen and at least one additional lumen for venting the area immediately adjacent the catheter. The vent lumen has multiple vent apertures provided along the length thereof to ensure thorough venting. Preferably, a third lumen fluidly connected to a pressure-sensing device is also integrally formed into the catheter. In practice, the distal end of the catheter is inserted through an access aperture formed in the aorta, passed through the aortic valve into the left ventricle. Pressurized fluid is injected into the left ventricle through the main lumen of the catheter. The fluid pressure within the left ventricle is monitored through the pressure-sensing lumen while the surgeon visually inspects the valve competency. The vents are utilized prior and subsequent to evaluating the competency of the valve for removing air and fluid from the area adjacent the catheter.

20 Claims, 4 Drawing Sheets

CATHETER AND METHOD FOR EVALUATING COMPETENCY OF MITRAL VALVE

BACKGROUND OF THE INVENTION

1. Field of the Invention

This invention relates to catheters intended to be inserted into the body and, more specifically, to a catheter and method for using the same for evaluating the competency of a mitral valve during cardiac surgery.

2. Description of the Related Art

The mitral valve is positioned in the heart between the left ventricle and left atrium and controls the flow of blood from the left atrium to the left ventricle. Under normal conditions, the valve permits the flow of blood from the atrium to the ventricle as the left atrium contracts. However, as the left ventricle begins to contract, a normal operating mitral valve closes to prevent the blood from returning to the left atrium. This reverse flow is known as regurgitation. As the left ventricle contracts, blood flows through the aortic valve into the aorta for distribution throughout the body.

One form of heart disease is deterioration or degradation of the valves, such as the mitral valve. It is often preferable to repair a natural valve rather than excising the valve and replacing it with a prosthesis or replacement tissue valve. A patient having a replacement valve such as a prosthetic valve must be placed on anti-coagulant drugs for the remainder of his or her life. However, a repaired valve which does not necessarily include any prosthetics or new tissue does not require this lifelong commitment to anti-coagulant drugs. In addition, valve repair surgery is often safer and less expensive than implantation of a prosthetic valve or tissue. In general, mitral valve repair preserves left ventricular function better than mitral valve replacement because during repair, the subvalvular papillary muscles and chordae tendineae are preserved whereas during mitral valve replacement, they cannot always be preserved in their natural orientation. Therefore, valve repair is often more desirable than replacement.

A significant concern for surgeons performing repairs of valves such as the mitral valve is confirming the competency of the valve repair prior to removing the patient from cardiac bypass. One known technique for evaluating the competency of a repaired mitral valve is to insert a catheter through the mitral valve and inject a suitable fluid, such as saline, into the left ventricle. The catheter is removed and the surgeon observes the competency of the valve. The surgeon can directly view the valve through the typical access aperture created in the heart wall for performing the mitral valve repair or replacement, namely, a surgical incision cut into the left atrium. One problem with this valve testing technique is the creation of insufficient fluid pressure within the ventricle to confidently evaluate the performance of the valve. In addition, this technique also requires insertion of the catheter through the mitral valve which can also distort the valve performance.

Another known technique for evaluating the competency of a repaired mitral valve is to create an incision in the left ventricle and insert one end of a catheter therethrough. A suitable fluid is injected, under pressure, into the left ventricle as the surgeon observes the competency of the mitral valve through the surgical access aperture created in the left atrium. A significant problem with this procedure is creating yet another incision in the wall of the heart. Any incision of the left ventricle is to be avoided because of potential healing problems in view of the significant fluid pressures naturally occurring inside this chamber.

SUMMARY OF THE INVENTION

The catheter for evaluating the competency of the mitral valve according to the invention overcomes these problems in that the catheter permits the creation of fluid pressure within the ventricle which approaches the mean-left ventricular pressure. In addition, the catheter accomplishes this without the creation of any extra incisions in the sidewall of the ventricle and without causing distortion of the mitral valve.

In one aspect, the invention is directed to a catheter for evaluating the competency of a heart valve comprising a catheter body, a fluid lumen formed in the catheter body, and a vent lumen formed in the catheter body. The fluid lumen has a proximal aperture intended to be positioned outside the heart and a distal aperture formed at a point on the catheter body so that the distal aperture can fluidly communicate with at least one of the heart chambers when the proximal aperture is positioned outside the heart. The vent lumen is similarly formed in the catheter body and has multiple apertures spaced along the length of the catheter body. With this structure, the catheter is adapted to be inserted into the heart chamber and deliver fluid thereto. In addition thereto, the heart chamber can be vented to remove unwanted fluids or gas during the test procedure therefrom.

In another embodiment, the catheter includes a pressure lumen formed in the catheter body. The proximal aperture of the pressure lumen is adapted to be fluidly connected to a pressure-sensing device, and a distal aperture of the pressure lumen is provided on the catheter body so that the distal aperture is received in the heart chamber when the proximal aperture is positioned outside the heart. With this structure, the fluid pressure immediately adjacent the distal end of the catheter body can be monitored.

In still another embodiment of the invention, a secondary fluid lumen is provided on the catheter body. The secondary fluid lumen has a proximal aperture which is intended to be connected to a source of cardioplegia solution. A distal aperture is formed in the catheter body and is intended to be received inside the aorta for the delivery of cardioplegia solution thereto.

In another aspect, the invention is directed to a method for evaluating the competency of a heart valve. First, a catheter substantially as described above is provided. Also provided is a fluid source fluidly connected to the proximal aperture of the fluid lumen and a suction source fluidly connected to the proximal aperture of the fluid lumen. The distal end of the catheter body is inserted into a heart chamber so that both the distal aperture of the fluid lumen and at least one of the vent lumen apertures are received inside the heart chamber. Next, the heart is either filled or emptied through the fluid lumen by either infusing or suctioning fluid. When the heart chamber receives fluid, the surgeon can inspect the valve to evaluate the competency of the valve.

In another embodiment of the invention, the distal end of the catheter is positioned in the aorta prior to inserting the distal end of the catheter into the heart chamber. Once the distal end of the catheter is positioned in the aorta, cardioplegia solution is delivered to the aorta through the fluid lumen. When the desired amount of cardioplegia solution has been delivered, then the distal end of the catheter is advanced into the heart chamber as previously described.

In still another embodiment of the method, a pressure-sensing lumen is provided in the catheter body, and a pressure-sensing device is fluidly connected to the lumen. The distal aperture of the pressure sensing lumen is provided in the catheter body at a point so that it will be received inside the heart chamber. The fluid pressure inside the heart chamber is measured through the pressure sensor.

In still yet another embodiment of the invention, a secondary fluid lumen is formed in the catheter body, and a source of cardioplegia solution is fluidly connected to the secondary lumen. The fluid outlet of the secondary lumen is positioned in the aorta, and cardioplegia solution is delivered from the source to the aorta through the secondary fluid lumen.

BRIEF DESCRIPTION OF THE DRAWINGS

The invention will now be described with reference to the drawings in which.

DETAILED DESCRIPTION OF THE PREFERRED EMBODIMENTS

Figure 1:
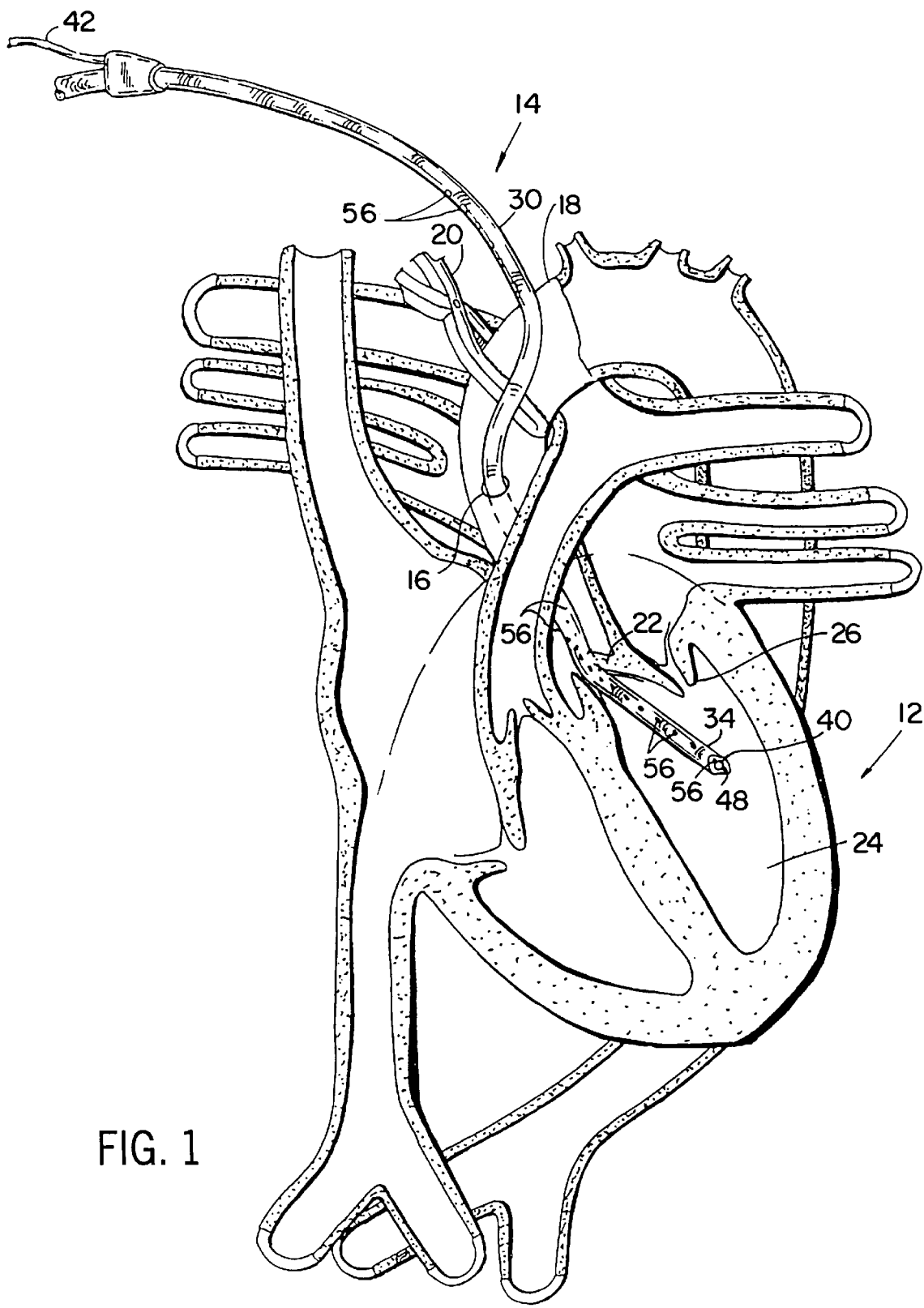
FIG. 1 is a schematic view of a human heart showing the evaluation catheter according to the invention positioned therein.
Figure 2:
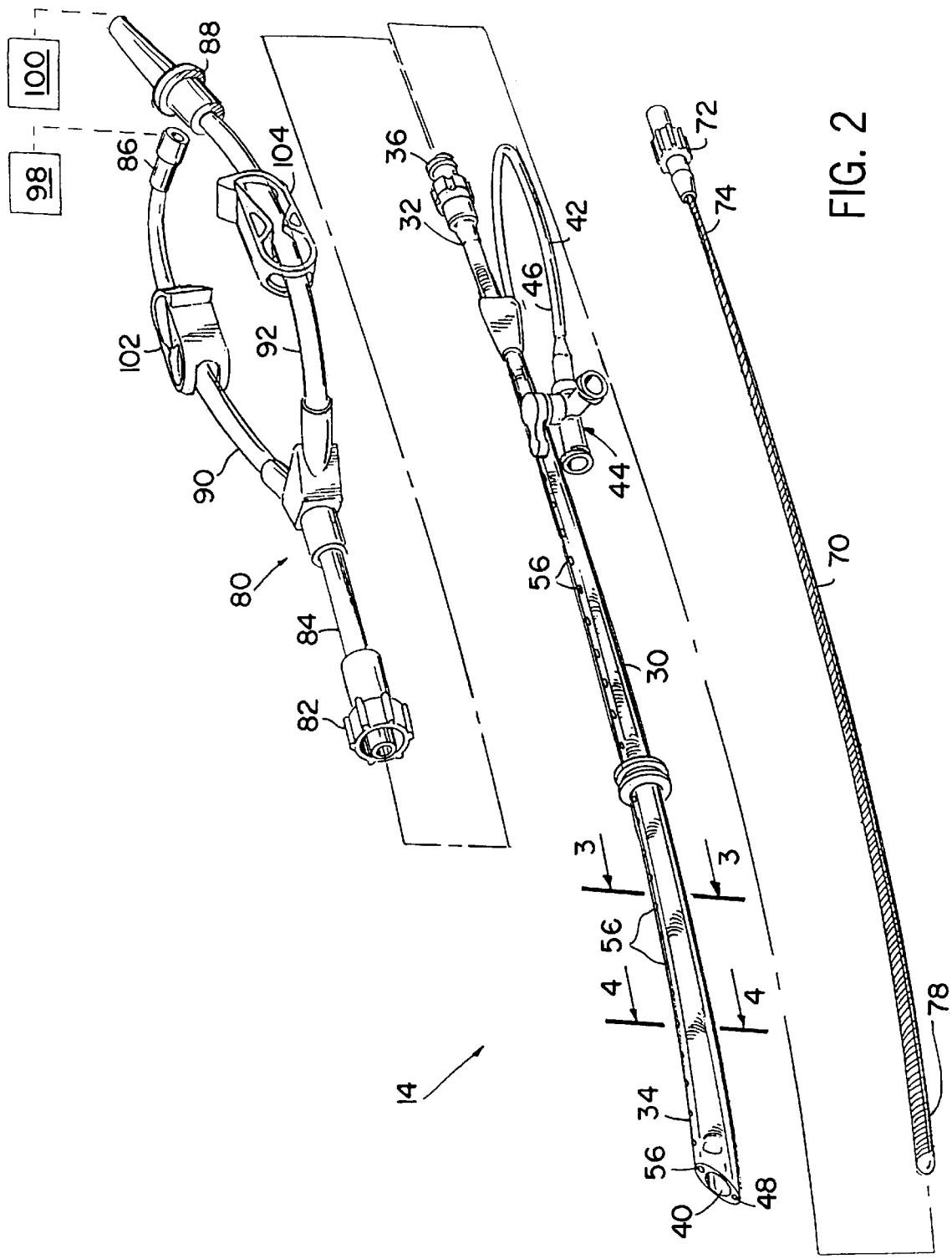
FIG. 2 is an exploded, perspective view of the evaluation catheter according to the invention.
Figure 3:
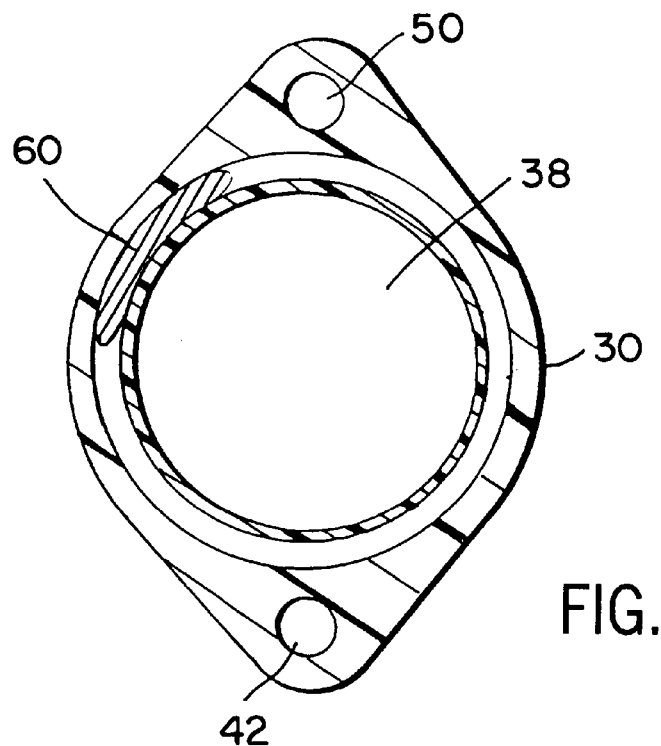
FIG. 3 is a sectional view taken along lines 3—3 of FIG. 2 showing the cross section of the catheter.
Figure 4:
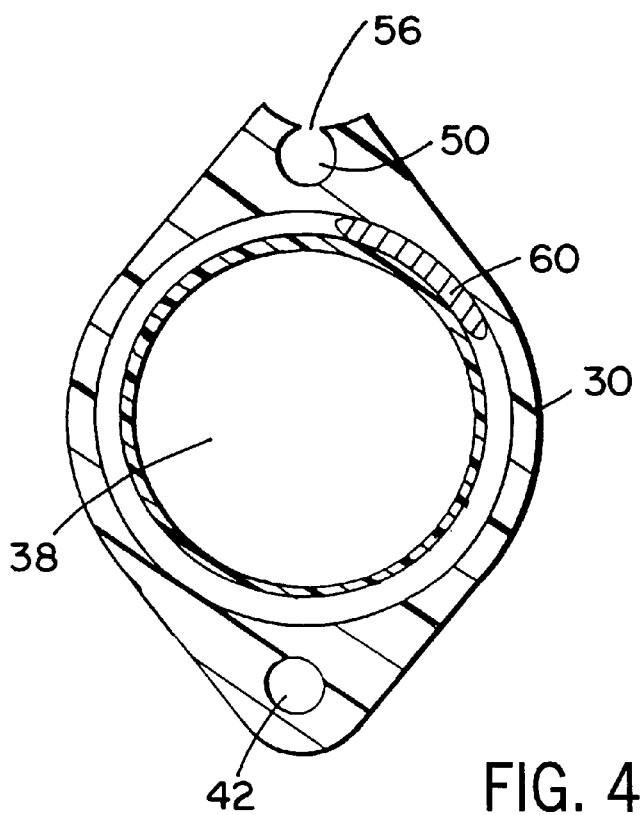
FIG. 4 is a cross-sectional view of the catheter taken along lines 4—4 of FIG. 2 showing the vent apertures of the vent lumen.

Referring now to the drawings, and to FIGS. 1–4 in particular, a heart 12 having a first embodiment of an evaluation catheter 14 received therein is shown. In the preferred embodiment, the evaluation catheter 14 is inserted through an incision 16 provided in the aorta 18 upstream from the clamp 20 used to close the aorta 18 during conventional bypass. The catheter 14 is inserted into the aorta 18 and directed through the aortic valve 22 so that at least a portion of the catheter 14 is received inside the left ventricle 24. In this position, the evaluation catheter 14 is ideally suited for evaluating the competency of the mitral valve 26. While this is the preferred embodiment of the invention, the evaluation catheter 14 can be used in any application throughout the body wherein selective venting and pressurization of a chamber or fluid-containing space are required.

The evaluation catheter 14 comprises a catheter body 30 having a proximal end 32 and a distal end 34. A conventional luer connector 36 is provided on the proximal end 32 of the catheter body 30. A main lumen 38 extends from the luer connector 36 to an outlet aperture 40 provided on the distal end 34 of the catheter body 30. The preferred embodiment of the evaluation catheter 14 also includes a pressure lumen 42 integrally formed into the catheter body. A conventional stopcock valve 44 is provided at the proximal end 46 of the pressure lumen 42, and an outlet aperture 48 is provided at the distal end of the pressure lumen 42.

A vent lumen 50 is also integrally formed into the catheter body 30. A vent aperture 56 is provided at the distal end of the vent lumen 50 and multiple vent apertures 56 are preferably spaced along a substantial portion of the length of the vent lumen 50. Incorporating multiple vent apertures 56 provides for venting of a relatively large area of the heart and surrounding vessels such as venting of multiple chambers of the heart and the root of the aorta using a single catheter. Preferably, the pressure lumen luer connector 44 is fluidly connected to a pressure-sensing device 62. Testing has shown that it is preferable to space the vent apertures 56 along the body of the catheter at intervals of approximately ½ centimeter. With this spacing, the heart chamber into which the catheter body is received can be effectively vented despite contact of the catheter with the heart wall, bending of the catheter, and the like. In addition, the catheter is preferably formed from easily deformable materials such as silicone or PVC.

In the preferred embodiment, the catheter body 30 is formed from silicone and is reinforced by a wire wound spring 60 which is integrally molded into the vent body. The spring 60 provides added resistance to bending of the flexible catheter body 30 without excessively limiting the flexibility.

The preferred embodiment of the catheter assembly according to the invention further includes an introducer 70 which is selectively received inside the main lumen 38 of the catheter body 30. The introducer 70 is formed of a flexible wire wound material which preferably provides added strength and rigidity to the catheter body 30 while still providing a limited amount of flexibility. The introducer 70 has a handle 72 provided on the proximal end 74 thereof. Preferably, the length of the introducer body 76 is dimensioned so that the distal end 78 of the introducer body 76 is positioned immediately adjacent the distal end 34 of the catheter body 30 when the introducer 70 is fully, telescopically received inside the main lumen 38. In practice, the introducer 70 is inserted into the main lumen 38 prior to inserting the catheter into the desired heart chamber. The evaluation catheter is inserted into the proper heart chamber, the introducer 70 is removed, and then the luer connector 36 of the main lumen 38 is interconnected to other apparatus for performing a variety of functions.

In the preferred embodiment, a Y-shaped adaptor 80 is mounted to the main lumen luer connector 36 after removal of the introducer 70. The Y-adaptor comprises a distal luer connector 82 provided at the terminal end of the primary conduit 84 and a pair of connectors 86, 88 which are mounted at the terminal end of a pair of secondary fluid conduits 90, 92. Preferably, a luer connector 86 is provided on the terminal end of the first secondary fluid conduit 90, and a suction connector 88 is provided on the second secondary fluid conduit 96. In operation, the luer connector 86 is connected to a source 98 of pressurized fluid, preferably saline, and the suction connector 88 is fluidly connected to a suction source 100. Conventional clamps 102, 104 are provided on the first and second secondary fluid conduits 90, 92, respectively, for selectively closing the conduits.

The preferred method of practicing the invention comprises providing an evaluation catheter 14 as described above with the introducer 70 inserted into the main lumen 38. Next, an acceptable incision 16 is cut into the aorta 18 upstream from the cross clamp 20. The distal end 34 of the catheter body 30 and introducer 70 are inserted into the aorta 18 through the incision 16 and threaded past the aortic valve 22 into the left ventricle. The catheter 14 is inserted a sufficient distance so that the outlet aperture 40 of the main lumen 38 and at least one vent aperture 56 are fully received inside the left ventricle 24. Preferably, the vent apertures 56 are spaced along the length of the vent lumen so that multiple vent apertures 56 are positioned inside the left ventricle, some of the vent apertures 56 are also positioned inside the aorta 18, adjacent the aortic root and some are positioned outside the heart and aorta.

Once the evaluation catheter is positioned as described above, the introducer 70 is removed from the catheter body 30, and the Y-adaptor 80 is secured to the main lumen luer connector 36. When the surgeon is ready to test the competency of the mitral valve, the pressure-sensing device 62 is activated and the stopcock valve 44 is opened. Next, the clamp 104 provided on the second secondary fluid conduit 92 is closed while the clamp 102 on the first secondary fluid conduit 90 is opened. Pressurized fluid is injected into the left ventricle 24 through the first secondary fluid conduit 90 and the main lumen 38. As the fluid flows into the left ventricle, the pressure-sensing device 62 evaluates the fluid pressure inside the left ventricle allowing the surgeon to monitor the fluid pressure therein. As the fluid enters the ventricle 24, the surgeon can measure the fluid pressure inside the ventricle 24 while observing the mitral valve 26 through the surgical incision formed in the left atrium. If the valve 26 is incapable of creating an effective fluid seal at normal pressure levels in the ventricle 24, then the surgeon can excise the mitral valve 26 and replace it with a suitable prosthesis or other acceptable valve replacement. However, if the surgeon observes an acceptable volume of fluid leaking or regurgitation through the mitral valve 26 into the left atrium, then the surgeon can have confidence in the repaired mitral valve.

In practice, testing has shown that the maximum fluid pressure created within the left ventricle 24 during testing should not exceed approximately 75 mm Hg. Preferably, an alarm or the like on the pressure-sensing device is calibrated at 75 mm Hg to prevent the creation of excessive, potentially damaging, fluid pressure inside the ventricle 24. Once the surgeon has visually observed the performance of the mitral valve 26, the application of pressurized fluid to the ventricle 24 is stopped by closing the clamp 102 provided on the first secondary fluid conduit 90. Immediately following this, the clamp 104 provided on the second secondary fluid conduit 92 is opened so that suction can be applied directly to the left ventricle 24 through the main lumen 38 for the purpose of removing the injected fluid.

After the injected fluids have been removed from the chambers of the heart and aorta, the evaluation catheter 14 is removed from the heart by withdrawing the catheter through the aortic incision 16. The aortic incision 16 is sutured closed, and finally, the patient can be taken off bypass in the conventional manner.

The preferred embodiment of the invention is used to evaluate the competency of the mitral valve. However, as is apparent to those skilled in the art, the evaluation catheter 14 according to the invention can be used to evaluate other valves in the heart and, alternatively, other fluid-containing chambers.

Figures 5, 6:
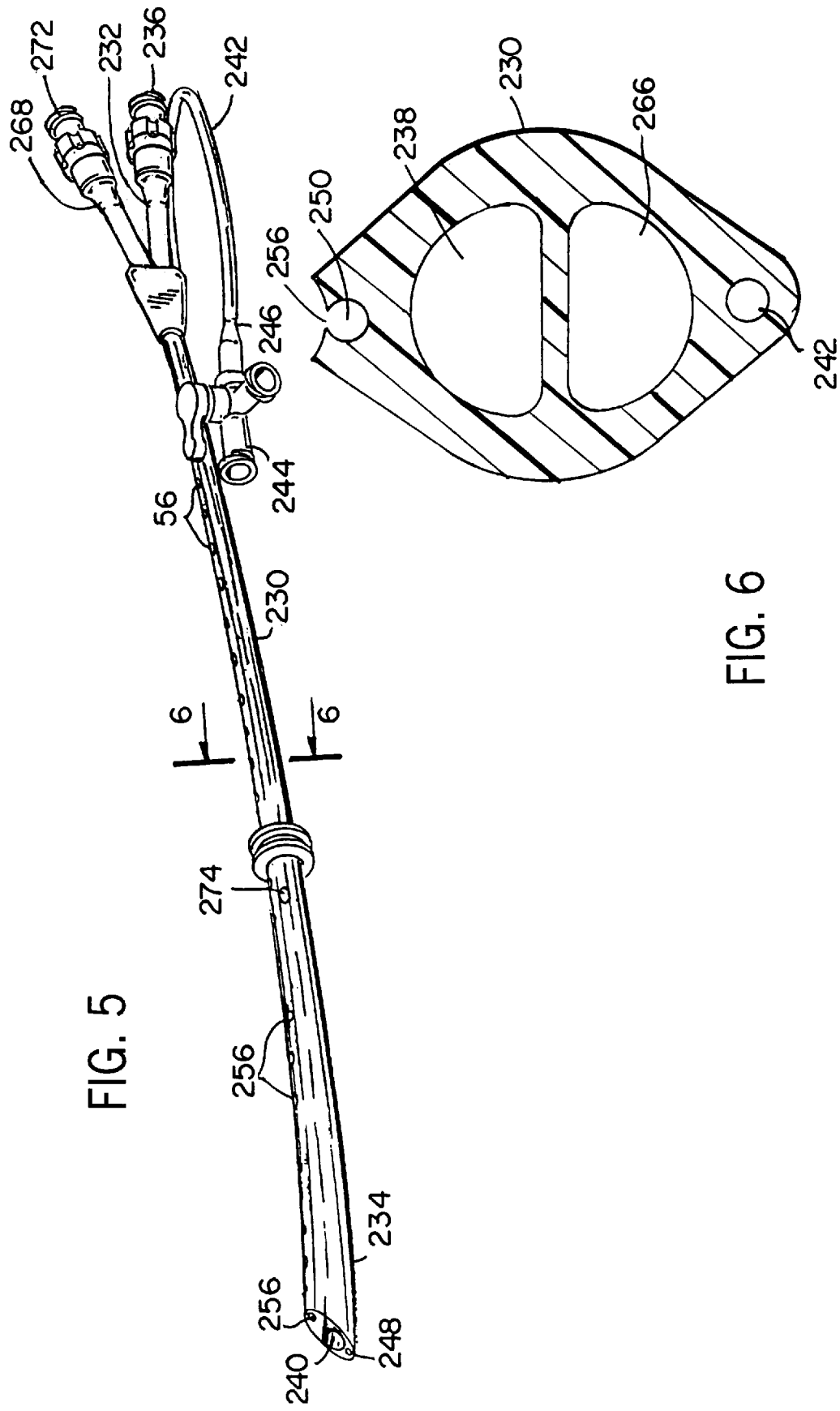
FIG. 5 is a perspective view of a second embodiment of the evaluation catheter according to the invention.
FIG. 6 is a sectional view taken along lines 6—6 of FIG. 5 showing the cross section of the second embodiment of the catheter.

A second embodiment of the evaluation catheter is seen in FIGS. 5 and 6. In describing the second embodiment, common elements of the first and second embodiments will share the same reference numerals, except that the reference numerals of the second embodiment will be increased by 200 from those used in describing the first embodiment. The second embodiment 214 of the evaluation catheter similarly comprises a catheter body 230 having proximal and distal ends 232, 234. In addition, the catheter body 230 includes a main lumen 238, a pressure lumen 242, and a vent lumen 250. In this embodiment, a perfusion lumen 266 is also integrally formed into the catheter body 230. The perfusion lumen 266 has a proximal end 268 and a distal end 270. A conventional luer connector 272 is provided on the proximal end 268, and the distal end 270 terminates at a fluid outlet aperture 274 provided a spaced distance from the distal end 234 of the catheter body 230. Preferably, the spacing of the fluid outlet aperture 274 from the distal end 234 is measured so that when the distal end 234 of the catheter body 230 is fully received and properly positioned within the left ventricle 24, the fluid outlet aperture 274 is received in the aorta 18 intermediate the aortic valve 22 and the incision 16. In this position, conventional cardioplegia solution can be forced through the perfusion lumen 266 and out the fluid outlet aperture 274 for antegrade perfusion of the heart through the coronary arteries. As is evident from the drawings, the remaining structure of the second embodiment is identical to that described above with respect to the first embodiment. In addition, the second embodiment of the catheter is used in the same manner as previously described.

The second embodiment of the evaluation catheter 214 is the preferred structure for performing the several functions of delivering cardioplegia solution to the coronary arteries and providing for venting of the heart chambers and evaluating the competency of the mitral valve. However, the first embodiment of the evaluation catheter 14 can be used in a different manner to accomplish the dual purposes of providing cardioplegia solution and evaluating the competency of the mitral valve. Specifically, the distal end 34 of the catheter body 30 can be initially inserted through the aortic incision 16 only a short distance so that the outlet aperture 40 of the main lumen 38 is positioned intermediate the incision 16 and the aortic valve 22. In this position, cardioplegia solution can be delivered to the coronary arteries through the main lumen 38. Because cardioplegia solution is typically applied only intermittently, the distal end 34 of the catheter body 30 can be advanced past the aortic valve 22 into the left ventricle 24 following the injection of cardioplegia solution into the aorta. Once the catheter 14 has been advanced into the ventricle 24, the ventricle can be vented by the vent lumen 50 and vent apertures 56 received therein. If additional cardioplegia solution is needed, then the catheter 14 can be partially withdrawn through the aortic incision 16 until the distal end 34 of the catheter body 30 is positioned intermediate the incision 16 and the aortic valve 22. Once again, in this position, cardioplegia solution can be delivered to the coronary arteries through the main lumen 38 and the aorta 18. After the necessary volume of cardioplegia solution has been delivered, the distal end 34 of the catheter body 30 can be advanced past the aortic valve 22 into the left ventricle 24 for continued venting of the ventricle and aorta. Once the catheter body has been positioned in the left ventricle, then the surgeon can evaluate the competency of the mitral valve 26 by injecting fluid as described above.

The several embodiments of the evaluation catheter according to the invention described above provide several advantages over the prior art in that the catheter provides an effective means for introducing fluid into the ventricle for evaluating the competency of the mitral valve while providing effective means for venting fluid chambers of the heart when the catheter is not being actively used for valve testing. In addition, the evaluation catheter according to the invention can be adapted for use to provide a method for supplying cardioplegia solution to the heart in addition to the previously described functions.

Reasonable variation and modification are possible within the spirit of the foregoing specification and drawings without departing from the scope of the invention.

The embodiments for which an exclusive property or privilege is claimed are defined as follows:

1. A catheter for evaluating the competency of a heart valve comprising:

a catheter body having proximal and distal ends;

a fluid lumen formed in the catheter body, the fluid lumen having a proximal aperture and a distal aperture, the distal aperture being formed at a point on the catheter body so that the distal aperture can fluidly communicate with at least one of the heart chambers when the proximal end is positioned outside the heart; and a vent lumen formed in the catheter body, the vent lumen having a proximal aperture adapted to be fluidly connected to the atmosphere, a distal aperture formed adjacent the distal end of the catheter body, and a plurality of body apertures provided intermediate the proximal and distal vent apertures;

wherein the catheter is adapted to be inserted into the heart chamber and deliver fluid thereto and also vent the heart chamber to remove unwanted fluids therefrom.

2. A catheter according to claim 1 and further comprising a pressure lumen provided in the catheter body, the pressure lumen having a proximal aperture adapted to be fluidly connected to a pressure sensing device and a distal aperture provided in the catheter body so that the distal aperture is received inside the heart chamber when the proximal aperture is positioned outside the heart.

3. A catheter according to claim 2 and further comprising a secondary fluid lumen provided in the catheter body, the secondary fluid lumen having a proximal aperture adapted to be fluidly connected to a source of cardioplegia solution and a distal aperture adapted to be received inside the aorta.

4. A catheter according to claim 3 wherein the distal aperture of the secondary fluid lumen is spaced from the distal end of the catheter body so that the distal aperture of the secondary fluid lumen is positioned in the aorta adjacent the coronary arteries when the distal end of the catheter body and the distal aperture of the vent lumen are received in the heart chamber.

5. A catheter according to claim 1 and further comprising a secondary fluid lumen provided in the catheter body, the secondary fluid lumen having a proximal aperture adapted to be fluidly connected to a source of cardioplegia solution and a distal aperture adapted to be received inside the aorta.

6. A catheter according to claim 5 wherein the distal aperture of the secondary fluid lumen is spaced from the distal end of the catheter body so that the distal aperture of the secondary fluid lumen is positioned in the aorta adjacent the coronary arteries when the distal end of the catheter body and the distal aperture of the vent lumen are received in the heart chamber.

7. A catheter according to claim 1 and further comprising a connector fluidly connected to the proximal aperture of the fluid lumen, the connector having a first fluid inlet adapted to be fluidly connected to a source of fluid and a second inlet adapted to be fluidly connected to a source of suction.

8. A catheter according to claim 1 wherein the plurality of vent lumen body apertures are spaced approximately one centimeter from one another.

9. A catheter according to claim 1 and further comprising an introducer comprising an introducer body having a distal end and a proximal end, the distal end and a substantial portion of the introducer body being adapted to be telescopically received in one of the several lumens of the catheter.

10. A method for evaluating the competency of a heart valve comprising the steps of:
providing a catheter comprising:
a catheter body having proximal and distal ends;
a fluid lumen formed in the catheter body, the fluid lumen having a proximal aperture and a distal aperture, the distal aperture being formed at a point on the catheter body so that the distal aperture can fluidly communicate with at least one of the heart chambers when the proximal end is positioned outside the heart; and a vent lumen formed in the catheter body, the vent lumen having a proximal aperture, a distal aperture formed adjacent the distal end of the catheter body, and a plurality of body apertures provided intermediate the proximal and distal vent apertures;

providing a fluid source fluidly connected to the proximal aperture of the fluid lumen;

fluidly connecting the vent lumen to the atmosphere;

inserting the distal end of the catheter body into a heart chamber so that both the distal aperture of the fluid lumen and at least one of the apertures of the vent lumen are received inside the heart chamber;

providing fluid to the heart chamber through the fluid lumen; and inspecting the valve when fluid has been supplied to the heart chamber.

11. The method of claim 10 wherein the heart chamber is vented prior to providing fluid to the heart chamber.

12. The method of claim 10 wherein the heart chamber is vented subsequent to providing fluid to the heart chamber.

13. The method of claim 10 and further comprising the steps of:
positioning the distal end of the catheter in the aorta prior to inserting the distal end of the catheter into the heart chamber; and
providing cardioplegia solution to the aorta through the fluid lumen.

14. The method of claim 10 and further comprising the steps of:
providing an introducer body having a distal end and a proximal end;
telescopically inserting the distal end and a substantial portion of the introducer body into one of the several lumens of the catheter prior to insertion of the catheter into the heart chamber; and
removing the introducer body from said one of the several lumens after the catheter has been positioned in the heart chamber.

15. The method of claim 10 and further comprising the steps of:
providing a pressure sensing lumen in the catheter body, the pressure sensing lumen having a proximal aperture adapted to be positioned outside the heart and a distal aperture adapted to be received inside the heart chamber;
providing a pressure sensing device fluidly connected to the pressure sensing lumen; and
measuring the fluid pressure inside the heart chamber through the pressure sensing lumen and the pressure sensor.

16. The method according to claim 10 and further comprising the steps of:
providing a secondary fluid lumen in the catheter body, the fluid lumen having a distal fluid outlet aperture and a proximal aperture;
providing a source of cardioplegia solution fluidly connected to the secondary fluid lumen;
positioning the fluid outlet aperture in the aorta; and
supplying cardioplegia solution from the source of cardioplegia solution to the aorta through the secondary fluid lumen.

17. The method according to claim 17 wherein the steps of supplying cardioplegia solution and venting the heart chamber are performed simultaneously.

18. A catheter assembly comprising:
   a catheter comprising:
      a catheter body having proximal and distal ends;
      a fluid lumen formed in the catheter body, the fluid lumen having a proximal aperture and a distal aperture, the distal aperture being formed at a point on the catheter body so that the distal aperture can fluidly communicate with at least one of the heart chambers when the proximal end is positioned outside the heart; and
      a vent lumen formed in the catheter body, the vent lumen having a proximal aperture adapted to be fluidly connected to the atmosphere, a distal aperture formed adjacent the distal end of the catheter body, and a plurality of body apertures provided intermediate the proximal and distal vent apertures; and
      a pressure lumen provided in the catheter body, the pressure lumen having a proximal aperture adapted to be fluidly connected to a pressure sensing device and a distal aperture adapted to be received inside the heart chamber; and
   an introducer having a distal end and a proximal end, the distal end and a substantial portion of the introducer body being adapted to be telescopically received in one of the several lumens of the catheter.

19. A catheter assembly according to claim 18 and further comprising a connector fluidly connected to the proximal aperture of the fluid lumen, the connector having a first fluid inlet adapted to be fluidly connected to a source of fluid and a second inlet adapted to be fluidly connected to a source of suction.

20. A catheter assembly according to claim 19 wherein the plurality of vent lumen body apertures are spaced approximately ½ centimeter from one another.

* * * * *